United States Patent [19]

Miller et al.

[11] Patent Number: 5,360,720
[45] Date of Patent: Nov. 1, 1994

[54] METHOD OF PREPARING HUMAN CONJUNCTIVAL MAST CELLS FOR MAST CELL STABILIZATION ASSAYS

[75] Inventors: Steven T. Miller, Arlington; John M. Yanni, Burleson, both of Tex.

[73] Assignee: Alcon Laboratories, Inc., Fort Worth, Tex.

[21] Appl. No.: 134,148

[22] Filed: Oct. 8, 1993

[51] Int. Cl.$^5$ .......................... C12Q 1/02; C12Q 1/00; G01N 33/53; G01N 33/567
[52] U.S. Cl. ...................................... 435/29; 435/7.21; 436/501; 436/503; 436/506; 436/507; 436/513; 436/519
[58] Field of Search ................... 435/29, 7.21; 436/501, 436/503, 506, 507, 513, 519; 530/387.1, 862, 868

[56] References Cited

U.S. PATENT DOCUMENTS 4,559,310 12/1985 Cantor et al. ..................... 436/519
4,740,371 4/1988 St. Remy ........................... 424/85

OTHER PUBLICATIONS

Schulman et al. "Human Lung Mast Cells: Purification & Characterization" J. Immunol. 129 (6) 2662–2667 1982.
Lowman et al. "Human Mast Cell Heterogeneity: Histamine Release from Mast Cells Dispersed from Skin, Lung, Adenoids, Tonsils & Colon in Response to IgE Dependent & Non Immunologic Stimuli" J Allergy Clin Immmunol. 81 (3) 590–597 1988.
Ite et al. "Mast Cell Heterogeneity: Functional Comparison of Purified Mouse Cutaneous & Peritoneal Mast Cells" J Invest. Dermatol 95 (2)178–185 1990.
Lawrence et al. "Purification & Characterization of Human Skin Mast Cells" J. Immunol. 139 (9) 3062–3069 1987.
Benyon et al. "Human Skin Mast Cells: Their Dispersion, Purification & Secretory Characterization" J Immunol 138 (3) 861–867 1984.
Massey et al. "Human Uteryie Mast Cells" J. Immunol. 147 (5) 1621–1627 1991.
Signa Catalog p. 764 Product #P 1644 1992.
Church, "Is Inhibition of Mast Cell Mediator Release Relevant to the Clinical Activity of Anti-allergic Drugs?," *Agents and Actions*, vol. 18, ¾, pp. 288–293 (1986).
Clegg et al., "Histamine Secretion from Human Skin Slices Induced by Anti-IgE and Artificial Secretagogues and the Effects of Sodium Cromoglycate and Salbutnol," *Clin. Allergy*, vol. 15, pp. 321–328 (1985).
Irani et al., "Mast Cell Heterogeneity," *Clinical and Experimental Allergy*, vol. 19, pp. 143–155 (1989).
Pearce et al., "Effect of Disodium Cromoglycate on Antigen Evoken Histamine Release in Human Skin," *Clinical Exp. Immunol.*, vol. 17, pp.437–440 (1974).
Schwartz et al., "Quantitation of Histamine, Tryptase, and Chymase in Dispersed Human T and TC Mast Cells," *J. Immunol.*, vol. 138, pp. 2611–2615 (1987).
Undem et al., "Comparative Studies of Mediator Release from Guinea Pig Lung Mast Cells and Basophils," *Am. Rev. Respir. Dis.*, vol. 133, pp. 763–768 (1986).
"The Lung," *Scientific Foundations*, Raven Press, Ltd., New York, Ch. 3.4.11 (1991).
Befus, A. D., Dyck, N., Goodacre, R., Bienenstock, J. Mast cells from the human intestinal lamina propria.

(List continued on next page.)

*Primary Examiner*—Jeffrey E. Russel
*Assistant Examiner*—Nancy J. Gromet
*Attorney, Agent, or Firm*—Patrick M. Ryan

[57] ABSTRACT

By allowing the mast cell enriched population of human conjunctival tissue cells to incubate for a minimum of about forty (40) hours post enzymatic digestion, the treatment window between spontaneous histamine release and anti-human IgE stimulated histamine release is increased. Culturing the human conjunctival tissue mast cells decreases the spontaneous release of histamine and increases the anti-IgE stimulated histamine release, greater than ten fold over spontaneous, at time points over forty (40) hours. This treatment window is sufficient to detect a compound's stabilizing or anti-allergic activity.

10 Claims, 1 Drawing Sheet

OTHER PUBLICATIONS

Isolation, histochemical subtypes and functional characterization. J. Immunol. 138(8):2604–2610, Apr. 1987.

Benyon, R. C., Robinson, C., Church, M. K. Differential release of histamine and eicosanoids from human skin mast cells activated by IgE-dependent and non-immunologic stimuli. Br. J. Pharmacology, (1989), 97:898–904.

Church, M. K., Pao, G. J-K., Holgate, S. T. Characterization of histamine secretion from mechanically dispersed human lung mast cells: Effects of anti-IgE, calcium ionophore A23187, compound 48/80 and basic polypeptides. J. Immunol. 129(5):2116–2121, Nov. 1982.

Fox et al., Isolation and Characterization of Human Intestinal Mucosal Mast Cells, J. Immunol. 135(1):483–491 (1985).

Kubota, Y., The Effect of Human Anaphylatoxins and Neutrophils on Histamine Release from Isolated Human Skin Mast Cells. J. Derm. 19:19–26 (1992).

Lewis, R. A., Soter, N. A., Diamond, P. T., Austen, K. F., Oates, J. A., Roberts, L. J. II Prostaglandin D2 generation after activation of rat and human mast cells with anti-IgE. J. Immunol. 129(4):1627–1631, Oct. 1982.

Peters, S. P., MacGlashan, D. W. Jr., Schulman, E. S., Schleimer, R. P., Hayes, E. C., Rokach, J., Adkinson, N. F. Jr. and Lichtenstein, L. M. Arachidonic acid metabolism in purified human lung mast cells. J. Immunol. 132(4):1972–1979, Apr. 1984.

Stellato, C., Cirillo, R., de Paulis, A., Casolaro, V., Patella, V., Mastronardi, P., Mazzarela, B. and Marone, G. Human basophil/mast cell releasability. IX Heterogeneity of the effects of opioids on mediator release. Anesthesiology, (1992), 77:932–940.

Tharp, M. D., Kagey-Sobotka, A., Fox, C. C., Marone, G., Lichtenstein, L. M., Sulluvan, T. J. Functional heterogeneity of human mast cells from different anatomic sites: In vitro responses to morphine sulfate. J. Allergy Clin. Immunol. 79(4):646–653, Apr. 1987.

Wardlaw, A. J., Cromwell, O., Celestino, D., Fitzharris, P., Geddes, D. M., Collins J. V. and Kay, A. B. Morphological and secretory properties of bronchoalveolar lavage mast cells in respiratory diseases. Clinical Allergy, 1986, 16:163–173.

Effect of Equilibration Time in Culture Medium on
Histamine Release From Human Conjunctival Tissue Mast Cells

METHOD OF PREPARING HUMAN CONJUNCTIVAL MAST CELLS FOR MAST CELL STABILIZATION ASSAYS

BACKGROUND

Mast cells differ between species. For example, it is now well established that the types of mast cells which exist in rodents are different from those in humans. See, for example, *THE LUNG: Scientific Foundations*, Raven Press, Ltd., New York, Ch. 3.4.11 (1991). Moreover, mast cell populations exist within the same species that differ in phenotype, biochemical properties, functional and pharmacological responses and ontogeny. These recognized differences in mast cells both between and within species are referred to as mast cell heterogeneity. See, for example, Irani et al., "Mast Cell Heterogeneity," *Clinical and Experimental Allergy*, Vol. 19, pp. 143-155 (1989). Because different mast cells exhibit different responses to pharmacological agents, it is not predictable that compounds claimed to be anti-allergic ("mast cell stabilizers") will have clinical utility in specific mast cell populations. The assumption that mast cells are a homogeneous population and that therefore experiments in rat mast cells would be predictive of those in human cells is known to be incorrect. Church, "Is Inhibition of Mast Cell Mediator Release Relevant to the Clinical Activity of Anti-Allergic Drugs?," *Agents and Actions*, Vol. 18, ⅔, 288-293, at 291 (1986).

Examples exist in the art in which mast cell stabilizing drugs inhibit only select populations of mast cells. Disodium cromoglycate is an anti-allergic drug whose local effects are believed to be due to inhibition of mast cell degranulation (Church, *Agents and Actions*, at 288). This drug was shown to inhibit rodent mast cell degranulation. In human trials, 100 μM of the drug inhibited mast cells obtained from bronchoalveolar lavage fluid. In dispersed human lung mast cell preparations, 1000 μM of the drug was required to inhibit only 25% to 33% of histamine release. Finally, histamine release from human skin mast cells was not inhibited at all by disodium cromoglycate. Pearce et al., "Effect of Disodium Cromoglycate on Antigen Evoked Histamine Release in Human Skin," *Clinical Exp. Immunol.*, Vol. 17, 437-440 (1974); and Clegg et al., "Histamine Secretion from Human Skin Slices Induced by Anti-IgE and Artificial Secretagogues and the Effects of Sodium Cromoglycate and Salbutanol," *Clin. Allergy*, Vol. 15, 321-328 (1985). These data clearly indicate that classification of a drug as an anti-allergic does not predict that the drug possess inhibitory effects on all mast cell populations.

Mast cell heterogeneity makes it desirable to test drug compounds for human conjunctival mast cell stabilizing activity using human conjunctival mast cells. Schwartz et al. have previously reported a method for obtaining monodispersed cell suspensions of human skin mast cells, *J. Immunol.*, Vol 138, 2611 (1987). This method uses an enzyme mixture composed of collagenase (30 mg), hyaluronidase (10 mg) and deoxyribonuclease I (3 mg) per digestion for tissue quantities up to 4 grams. These quantities of enzymes calculate to approximately 13000 U collagenase, 3500 U hyaluronidase and 6000 U deoxyribonuclease I per digestion. Experiments conducted using this dispersion method yield cell suspensions of initially low viability (<50%) when applied to human conjunctival tissue. Enrichment of the cell suspension for mast cells using a 30% Percoll ® cushion yielded about a 4 to 5 fold increase in the number of mast cells. These cells were still functional as assessed by calcium ionophore $A_{23187}$ stimulation (40-80% of total histamine release was elicited with 10 μM $A_{23187}$). However, the spontaneous release of histamine from these preparations was unacceptably high (>10% of total release) while the stimulated release of histamine using anti-human IgE (10 μg/ml) was low (10 to 18% of total histamine release). Consequently, the treatment window between spontaneous and stimulated release was not sufficiently large enough to assess the activity of test compounds on histamine release from the mast cells.

Undem et al. have previously reported a method for obtaining monodispersed cell suspensions containing guinea pig lung mast cells. *Am. Rev. Respir. Dis.*, Vol 133, 763-768 (1986). This method uses enzymes selected for the lung tissue but much lower concentrations of collagenase (125 U) per digestion per gram of tissue were employed. When concentrations of collagenase and hyaluronidase are adjusted down to concentrations more consistent with these levels, 200 U each per enzyme per digestion per gram of tissue, the viability of the post digestion populations increased to 70-80%. After enrichment using a 30% Percoll ® cushion, the viabilities improved to >95% though the numbers of mast cells were small (approximately 3%; typically <100,000 mast cells). Cells obtained through the low concentration enzyme treatment were functional as assessed by calcium ionophore $A_{23187}$ stimulation (45% of total histamine release was elicited with 10 μM $A_{23187}$). Spontaneous release of histamine was approximately 10% of total release. Anti-human IgE stimulated histamine release was improved to approximately 20% of total release but still was not sufficient to provide a large treatment window.

Additional treatment of the intact tissues from these digestions with collagenase and hyaluronidase at the much higher "Schwartz" levels (above) yielded greater numbers of mast cells (3-16 times greater than that already obtained through 200 U treatments). Viability of these cells post Percoll ® enrichment was greater than 95%. Cells obtained with these additional treatments were functional as assessed by calcium ionophore $A_{23187}$ stimulation (40% of total release was elicited with 10 μM $A_{23187}$). Moreover, these cells tend to yield lower spontaneous release levels (6%) but also lower total histamine release levels. Anti-human IgE stimulated histamine release was 15% of total release and still not sufficient to provide a large treatment window.

Accordingly, a need exists for an improved method of preparing human conjunctival mast cells for mast cell stabilization assays.

SUMMARY OF THE INVENTION

An improved method of preparing human conjunctival mast cells for use in mast cell stabilization assays and evaluation of antiallergic drugs has now been found. The improved method of the present invention thus comprises the steps of:
(a) Enzymatically digesting human conjunctival tissue;
(b) washing the tissue of step (a) with a buffer over a filter so that the filtrate is collected;
(c) enriching the filtrate of step (b) for mast cells;
(d) forming a mast cell preparation by resuspending the enriched cells in a buffer;

(e) allowing the mast cell preparation to equilibrate at about 30°-37° C. in a culture medium supplemented with at least serum and non-stable essential amino acids for a minimum of about 40 hours;

(f) harvesting the mast cells from the culture medium; and (g) determining viability and number of mast cells.

Among other factors, the present invention is based on the finding that allowing the isolated conjunctival mast cells to equilibrate at about 30°-37° C. for a minimum of about 40 hours in a culture medium prior to treatment or challenge permits the treatment window between spontaneous and stimulated histamine release to be great enough to detect significant decreases in histamine release levels from cells treated with test compound prior to immunologic challenge with anti-human IgE.

DETAILED DESCRIPTION OF THE INVENTION

Tissue

Figure 1:
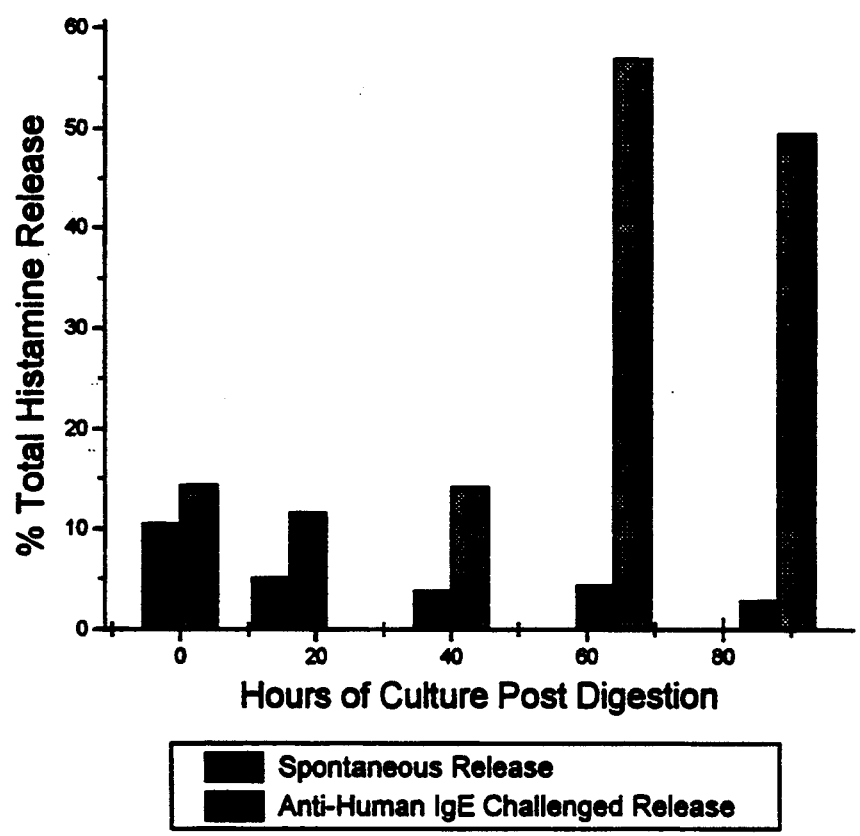
FIG. 1 compares spontaneous and immunologically challenged histamine release with increasing mast cell culture time.

Human conjunctival tissue is obtained from organ/tissue donors. The tissue may be stored in a suitable culture medium in glass or plastic vials (approximately 20 mL in size) and refrigerated until needed. Suitable culture media include, but are not limited to, RPMI 1640, Minimum Essential Medium (MEM), Dulbecco's Modified Eagle Medium (D-MEM), and CMRL Media. Suitable culture media may also include more defined media such as Opti-MEM ® I Reduced Serum Media. Additionally, the culture media should be supplemented with serum and non-stable essential amino acids. The culture media may also be supplemented with antibiotics, fungicides, and biological buffers. The culture medium is preferably RPMI 1640 supplemented with fetal bovine serum (20%), L-glutamine (2 mM), penicillin (100 units/ml), streptomycin (100 µg/ml), amphotericin B (2.5 µg/ml), and HEPES (10 mM). Preferably, tissue is stored refrigerated in a supplemented RPMI 1640 culture medium then incubated overnight at 37° C. prior to enzymatic digestion.

Preparation of Cell Suspension

Tissue is transferred from the culture medium to a suitable buffer for enzymatic treatment. Suitable buffers include, but are not limited to, Tyrode's, Hanks' Balanced Salt Solution (HBSS), and Earle's Balanced Salt Solution (EBSS). Preferably, the buffer is Tyrode's buffer (in mM: NaCl 137, KCl 2.7, $NaH_2PO_4$ 0.35, $CaCl_2$ 1.8, $MgCl_2$ 0.98, Na $HCO_3$ 11.9, glucose 5.5) containing 0.1% gelatin (TGCM).

Enzymatic digestion is preferably accomplished in two stages. During the first stage, the tissue is incubated with a relatively small amount of enzyme or enzyme mixture. Preferably, the enzyme treatment is a mixture of 200 U of collagenase (Type IV) and hyaluronidase (Type I-S) per gram of tissue for 30 minutes at 37° C. Following this first stage of enzymatic treatment, the tissue is washed with buffer over a filter and the filtrate is collected. Preferably the filter is a filter cloth.

Intact tissue is then placed in buffer for second stage digestion. This second stage digestion is more severe than the first. The enzyme or enzyme mixture is on the order of ten times the first stage. Preferably, the second stage digestion consists of incubating the tissue with 2000 U each of collagenase and hyaluronidase per gram of tissue for 30 minutes at 37° C. The tissue is then washed with buffer over a filter, preferably a filter cloth, and the filtrate collected.

The filtrate obtained from each digestion is centrifuged and the pelleted cells resuspended in buffer, preferably calcium/magnesium free buffer. Pooled cells from all digestions are then enriched for mast cells. Known methods of cell separation/enrichment include continuous or discontinuous gradient centrifugation and positive or negative selection through panning. Preferably, the enrichment/cell separation method is a discontinuous one band gradient of cell separation media, such as Percoll ® (collodial polyvinylpyrrolidone coated silica for cell separation, commercially available from Sigma Chemical Co., St. Louis, Mo.), Ficoll hypaque ®, Metrizamide ®, or bovine serum albumin. Most preferred is a single band of Percoll ® of about 1.058 g/L. Enriched mast cells are resuspended and washed in buffer.

Equilibration Prior to Treatment or Challenge

The preparations containing the mast cells are then placed in a culture medium, preferably supplemented RPMI 1640, and allowed to equilibrate at about 30°-37° C. for a minimum of about 40 hours. Equilibrating for less than about 40 hours does not provide a treatment window great enough to detect significant decreases in histamine release levels from cells treated with test compound prior to immunologic challenge with anti-human IgE.

After equilibrating for a minimum of about 40 hours, the cells may be harvested from the culture (for example, by gentle flushing utilizing pasteur pipets), pooled and centrifuged. Cell pellets may then be resuspended in buffer and viability and mast cell number determined by well known methods. The conjunctival mast cells are now prepared for use in mast cell stabilization assays.

Example 1—No Equilibrating Incubation in Culture Medium Prior to Treatment or Challenge Human conjunctival tissues are obtained from organ/tissue donors within 8 hours post death and placed in transport medium (typically Dexsol ® Corneal Transport Medium or equivalent). Upon receipt, tissues are weighed and placed in 20 mL screw capped glass vials or equivalent containing RPMI 1640 culture medium supplemented with fetal bovine serum (20%), L-glutamine (2 mM), penicillin (100 units/ml), streptomycin (100 µg/ml), amphotericin B (2.5 µg/ml), and HEPES (10 mM). Tissues are stored in supplemented RPMI 1640 medium up to about 5 days post death at 4° C. Prior to enzymatic digestion, tissues and culture medium are transferred to sterile petri dishes and incubated overnight at 37° C. (5% $CO_2$).

Tissues are transferred to Tyrode's buffer (in mM: NaCl 137, KCl 2.7, $NaH_2PO_4$ 0.35, $CaCl_2$ 1.8, $MgCl_2$ 0.98, $NaHCO_3$ 11.9, glucose 5.5) containing 0.1% gelatin (TGCM) for enzymatic treatment. Tissues are incubated with 200 U each of collagenase (Type IV) and hyaluronidase (Type I-S) per gram of tissue in an approximate volume of 20 mL for 30 minutes at 37° C. with mild agitation. Following enzyme digestion, tissues were washed with an equal volume of TGCM over Nitex ® filter cloth (100 µM mesh). Intact tissues were placed in TGCM for further enzymatic digestions. Two digestions were completed as described (Stage 1) and were followed by additional digestion steps (typically 3 to 5) using 2000 U each of collagenase and hyaluronidase per gram of tissue in an approximate volume of 20 mL for 30 minutes at 37° C. with mild agitation (Stage 2).

The filtrate obtained from each digestion was centrifuged (825 g, 7 minutes) and pelleted cells were resuspended in calcium/magnesium free Tyrode's buffer (TG). Pooled cells from all digestions were centrifuged (825 g, 30 minutes) over a 1.058 g/L Percoll ® cushion. Mast cell enriched cell pellets were resuspended and washed in TG buffer. Viability and number of mast cells were determined using trypan blue exclusion and toluidine blue O (50 mg toluidine blue O stain dissolved into the following solution: physiological saline, 39 mL; glacial acetic acid, 1 mL; formaldehyde (37%), 10 mL; ethanol (100%), 50 mL) staining of the harvested cell suspensions.

Cell suspensions containing 5000 mast cells were added to TGCM containing tubes and challenged with anti-human IgE (goat derived IgG antibody) for 15 minutes at 37° C. in a shaking waterbath. Challenge was terminated by centrifugation (500 g, 7 minutes). Supernatants were collected and stored (−20° C.) until histamine analysis. Total histamine release was obtained by exposing the cells to 0.1% Triton X-100. Spontaneous histamine release was obtained with TGCM only treatment. Non-specific, antibody stimulated release of histamine was addressed using normal goat serum (NGS) or goat IgG (Gt IgG). Histamine determinations were made by radioimmunoassay (AMAC, Inc., Westbrook, Me.).

| Treatment | % Total Histamine Release | | | |
|---|---|---|---|---|
| | 1 | 2 | 3 | 4 |
| Spontaneous Release: | 7.6 | 12.4 | 13.6 | 8.4 |
| anti-human IgE (10 μg/ml) | 10.3 | 15.6 | 16.8 | 14.5 |
| non-specific (NGS) | 5.4 | 1.4 | 0.6 | 6.3 (Gt IgG) |

Example 2—Less than 40 hour Equilibrating Incubation in Culture Medium Prior to Treatment or Challenge Cells were obtained as described in Example 1. Following the enrichment of mast cells over the Percoll ® cushion, the cells were counted for viability and number of mast cells as described and placed in 24-well culture plate containing 1 mL of supplemented RPMI 1640 culture medium (previously described) for overnight incubation. Following incubation (approximately 16 hours), the cells are harvested off the culture plate by gentle flushing using pasteur pipets, pooled and centrifuged (825 g, 7 minutes). Cell pellets were resuspended in TGCM and viability and number of mast cells were determined. Cells were challenged as described previously.

| Treatment | % Total Histamine Release |
|---|---|
| Spontaneous Release: | 5.1 |
| anti-human IgE (10 μg/ml) | 11.6 |
| non-specific (Gt IgG) | 5.5 |

Example 3—Forty Hour Equilibrating Incubation in Culture Medium Prior to Treatment or Challenge Cells were obtained and challenged as in Example 2 with the exception of approximately 40 hours of equilibrating incubation separating dispersion and challenge.

| Treatment | % Total Histamine Release |
|---|---|
| Spontaneous Release: | 3.8 |
| anti-human IgE (10 μg/ml) | 14.2 |
| non-specific (Gt IgG) | 15.3 |

Examples 4 and 5—Greater than Forty Hour Equilibrating Incubation in Culture Medium Prior to Treatment or Challenge Cells were obtained and challenged as in Example 2 with the exception of approximately 64 or 88 hours of equilibrating incubation separating dispersion and challenge.

Example 4

| Treatment | % Total Histamine Release | | | | | | |
|---|---|---|---|---|---|---|---|
| 64 Hours Culture | 1 | 2 | 3 | 4 | 5 | 6 | 7 |
| Spontaneous Release: | 3.4 | 5.6 | 3.0 | 5.0 | 3.2 | 5.7 | 4.8 |
| anti-human IgE (10 μg/ml) | 80.5 | 72.5 | 45.1 | 47.5 | 53.2 | 56.9 | 42.9 |
| non-specific (Gt IgG) | 3.8 | 5.3 | 3.6 | 5.2 | 2.9 | 5.2 | 4.4 |

Example 5

| Treatment | % Total Histamine Release | | |
|---|---|---|---|
| 88 Hours Culture | 1 | 2 | 3 |
| Spontaneous Release: | 2.5 | 1.8 | 4.3 |
| anti-human IgE (10 μg/ml) | 54.1 | 44.4 | 50.4 |
| non-specific (Gt IgG) | 2.5 | — | 4.3 |

By allowing the mast cell enriched population of human conjunctival tissue cells to incubate for a minimum of about forty (40) hours post enzymatic digestion, the treatment window between spontaneous histamine release and anti-human IgE stimulated histamine release is increased. As demonstrated in FIG. 1, culturing the human conjunctival tissue mast cells decreases the spontaneous release of histamine and increases the stimulated histamine release, greater than ten fold over spontaneous, at time points over forty (40) hours. This treatment window is sufficient to detect a compound's stabilizing or anti-allergic activity.

We claim:

1. A method of preparing human conjunctival mast cells for use in mast cell stabilization assays and evaluation of antiallergic drugs comprising the steps of:
   (a) enzymatically digesting human conjunctival tissue;
   (b) washing the tissue of step (a) with a buffer over a filter so that the filtrate is collected;
   (c) enriching the filtrate of step (b) for mast cells;
   (d) forming a mast cell preparation by resuspending the enriched cells in a buffer;
   (e) allowing the mast cell preparation to equilibrate at about 30°–37° C. in a supplemented tissue culture medium comprising serum and non-stable essential amino acids for a minimum of about 40 hours;

(f) harvesting the mast cells from the culture medium; and (g) determining viability and number of mast cells.

2. The method of claim 1 wherein the filtrate is enriched in stpe (C) by centrifugation over a Percoll® cushion of about 1.058 g/L.

3. The method of claim 1 wherein the buffer is Tyrode's buffer containing 0.1% gelatin.

4. The method of claim 1 wherein the culture medium is supplemented with serum, non-stable essential amino acids, an antibiotic, a fungicide, and a biological buffer.

5. The method of claim 4 wherein the culture medium is RPMI 1640 supplemented with fetal bovine serum (20%), L-glutamine (2 mM), penicillin (100 units/ml), streptomycin (100 µg/ml), amphotericin B (2.5 µg/ml), and HEPES (10 mM).

6. The method of claim 1 wherein the enzymatic digestion is accomplished with a mixture of collagenase (Type IV) and hyaluronidase (Type I-S).

7. The method of claim 1 wherein the enzymatic digestion in step (a) is accomplished in two stages.

8. The method of claim 7 wherein the amount of enzyme per gram of tissue in the first stage is about 200 U each of collagenase (Type IV) and hyaluronidase (Type I-S), and the amount of enzyme per gram of tissue in the second stage is about 2000 U each of collagenase (Type IV) and hyaluronidase (Type I-S).

9. The method of claim 1 wherein the mast cell preparation is allowed to equilibrate for a minimum of about 60 hours.

10. A method of preparing human conjunctival mast cells for use in mast cell stabilization or anti-allergic activity assays comprising the steps of:

(a) enzymatically digesting human conjunctival tissue using about 200 U each of collagenase (Type IV) and hyaluronidase (Type I-S) per gram of tissue;

(b) washing the human conjunctival tissue of step (a) with Tyrode's buffer containing 0.1% gelatin over a filter so that some intact tissue remains on top of the filter and the filtrate is collected;

(c) further enzymatically digesting the intact human conjunctival tissue of step (b) using about 2000 U each of collagenase (Type IV) and hyaluronidase (Type I-S);

(d) washing the intact human conjunctival tissue of step (c) with Tyrode's buffer containing 0.1% gelatin over a filter so that the filtrate is collected;

(e) centrifuging the filtrate of steps (b) and (d) over a Percoll® cushion of about 1.058 g/L to form pelleted cells;

(f) forming a mast cell preparation by resuspending the pelleted cells in Tyrode's buffer containing about 0.1% gelatin;

(g) allowing the mast cell preparation to equilibrate at about 30°–37° C. in a culture medium of RPMI 1640 supplemented with fetal bovine serum (20%), L-glutamine (2 mM), penicillin (100 units/ml), streptomycin (100 µg/ml), amphotericin B (2.5 µg/ml), and HEPES (10 mM) for a minimum of about 60 hours;

(h) harvesting the mast cells from the culture medium; and (i) determining viability and number of mast cells.

* * * * *